(12) United States Patent
Mansour et al.

(10) Patent No.: US 12,109,396 B2
(45) Date of Patent: *Oct. 8, 2024

(54) DUAL-CHAMBER SYRINGE WITH DUAL-LUMEN INTRAVENOUS SET

(71) Applicant: CareFusion 303, Inc., San Diego, CA (US)

(72) Inventors: George Mansour, Diamond Bar, CA (US); Eugene Mason, La Habra Heights, CA (US); Ryan Callahan, Long Beach, CA (US); Todd Oda, Torrance, CA (US); Wesley Underwood, La Habra, CA (US); Adel Shams, Brea, CA (US); Dylan Beyhl, Scottsdale, AZ (US); Seyed Salehi Borojerdi, Aliso Viejo, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/845,392

(22) Filed: Jun. 21, 2022

(65) Prior Publication Data

US 2022/0323677 A1 Oct. 13, 2022

Related U.S. Application Data

(63) Continuation of application No. 16/598,945, filed on Oct. 10, 2019, now Pat. No. 11,395,879.
(Continued)

(51) Int. Cl.
*A61M 5/19* (2006.01)
*A61M 5/28* (2006.01)
(Continued)

(52) U.S. Cl.
CPC .............. *A61M 5/19* (2013.01); *A61M 5/284* (2013.01); *A61M 2005/1787* (2013.01); *A61M 2005/3132* (2013.01)

(58) Field of Classification Search
CPC ...... A61M 5/19; A61M 5/284; A61M 5/2066; A61M 5/2448; A61M 2005/1787;
(Continued)

(56) References Cited

U.S. PATENT DOCUMENTS 2,677,374 A * 5/1954 Burnside ................. A61M 5/28
604/199
4,946,448 A 8/1990 Richmond
(Continued)

FOREIGN PATENT DOCUMENTS

EP 2168619 A2 3/2010
EP 2425870 A1 3/2012
(Continued)

OTHER PUBLICATIONS

Extended European Search Report for Application No. 22202447.3 dated Feb. 2, 2023, 7 pages.
(Continued)

*Primary Examiner* — Chelsea E Stinson
*Assistant Examiner* — Hong-Van N Trinh
(74) *Attorney, Agent, or Firm* — Morgan, Lewis & Bockius LLP

(57) ABSTRACT

A dual-chamber syringe may include an end wall and a primary plunger. The primary plunger may include a primary stopper. The primary stopper may form a primary chamber with the end wall. A secondary plunger may be in mechanical association with the primary plunger. The secondary plunger may include a secondary stopper. The secondary stopper may form a secondary chamber with the primary stopper. A primary nozzle may extend from the end
(Continued)

wall and may be in fluid communication with the primary chamber. A secondary nozzle may extend from the end wall and may be in fluid communication with the secondary chamber.

11 Claims, 15 Drawing Sheets

Related U.S. Application Data

(60) Provisional application No. 62/744,500, filed on Oct. 11, 2018.

(51) Int. Cl.
*A61M 5/178* (2006.01)
*A61M 5/31* (2006.01)

(58) Field of Classification Search
CPC .............. A61M 5/1407; A61M 5/1408; A61M 2005/3132; A61M 5/3134; A61M 5/31501
See application file for complete search history.

(56) References Cited

U.S. PATENT DOCUMENTS

| | | | |
|---|---|---|---|
| 5,396,925 A | 3/1995 | Poli | |
| 5,865,804 A * | 2/1999 | Bachynsky | A61M 5/2033 604/233 |
| 6,089,272 A | 7/2000 | Brand et al. | |
| 2004/0122418 A1 | 6/2004 | Voorhees | |
| 2008/0147012 A1 | 6/2008 | Rome et al. | |
| 2010/0327007 A1 * | 12/2010 | Fransson | A61M 5/31596 222/1 |
| 2011/0009837 A1 | 1/2011 | Schreiner | |
| 2012/0136298 A1 * | 5/2012 | Bendix | A61M 5/31515 29/428 |
| 2013/0274716 A1 | 10/2013 | Nelson et al. | |
| 2014/0121647 A1 | 5/2014 | Kirk | |
| 2015/0250952 A1 | 9/2015 | Naftalovitz et al. | |

FOREIGN PATENT DOCUMENTS

| | | | | |
|---|---|---|---|---|
| EP | 3243549 A1 | | 11/2017 | |
| JP | 2004129695 A | * | 4/2004 | ............ A61M 5/284 |
| JP | 2015523867 A | | 8/2015 | |
| JP | 2015211873 A | | 11/2015 | |
| WO | WO-8606967 A1 | | 12/1986 | |
| WO | WO-2017114921 A1 | | 7/2017 | |

OTHER PUBLICATIONS

International Preliminary Report on Patentability from the International Preliminary Examining Authority for Application No. PCT/US2019/055701, dated Oct. 2, 2020, 12 pages.
International Search Report and Written Opinion for Application No. PCT/US2019/055701, dated Mar. 17, 2020, 16 pages.
Invitation to Pay Additional Fees and Partial Search Report for Application No. PCT/US2019/055701, dated Jan. 24, 2020, 11 pages.
Japanese Office Action for Application No. 2021-519795, dated Jul. 26, 2023, 4 pages including translation.
Equashield, Equashield Product Brochure Page, date unknown, 1 page.
Japanese Office Action for Application No. 2023-195625, dated Jul. 4, 2024, 4 pages including translation.

\* cited by examiner

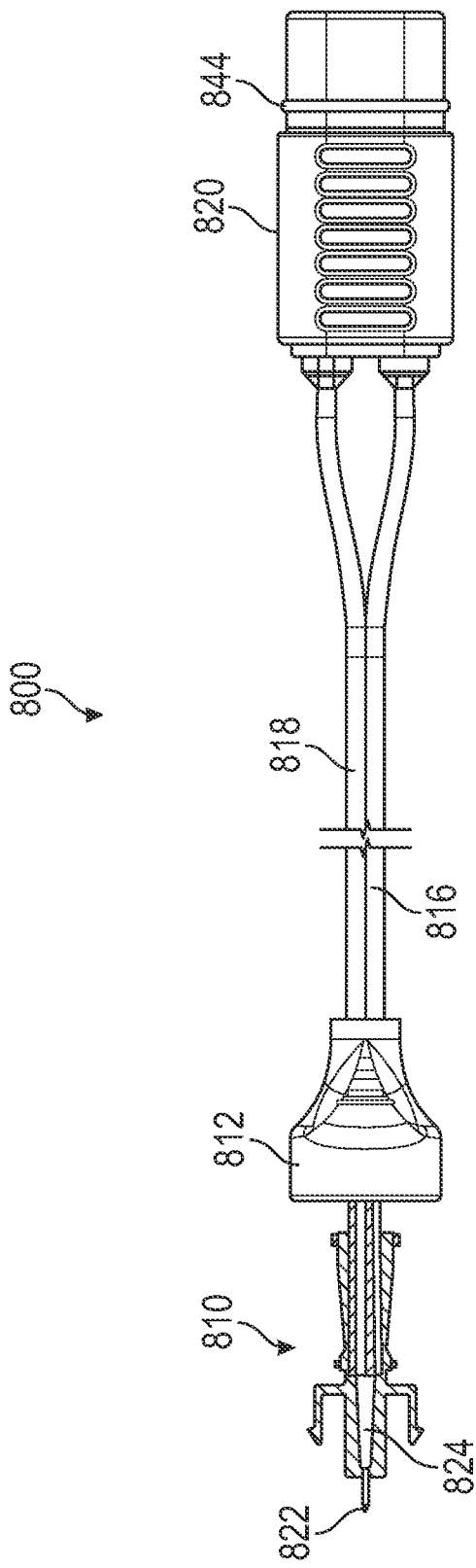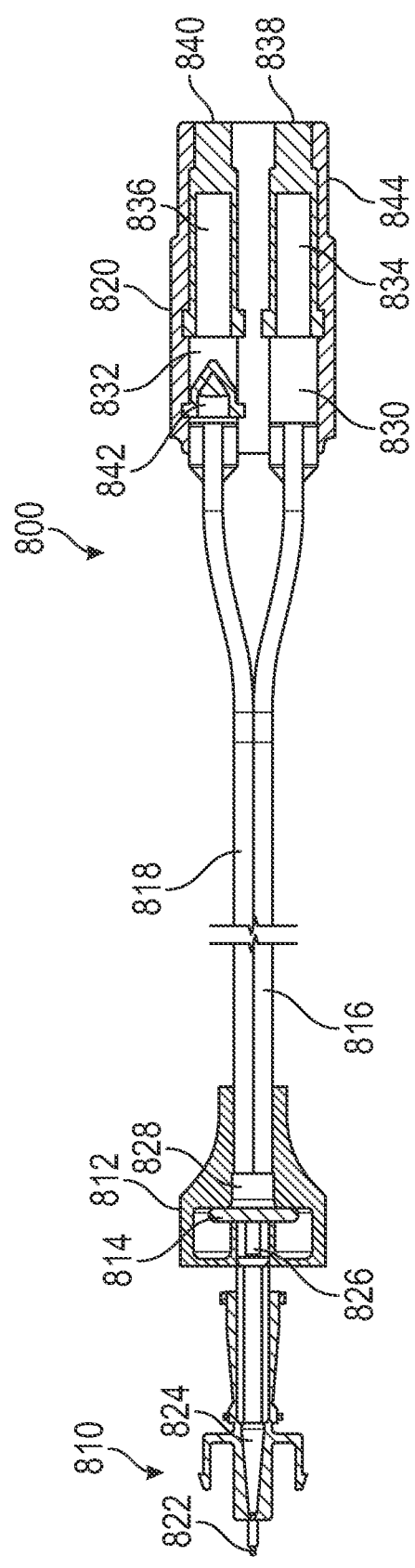

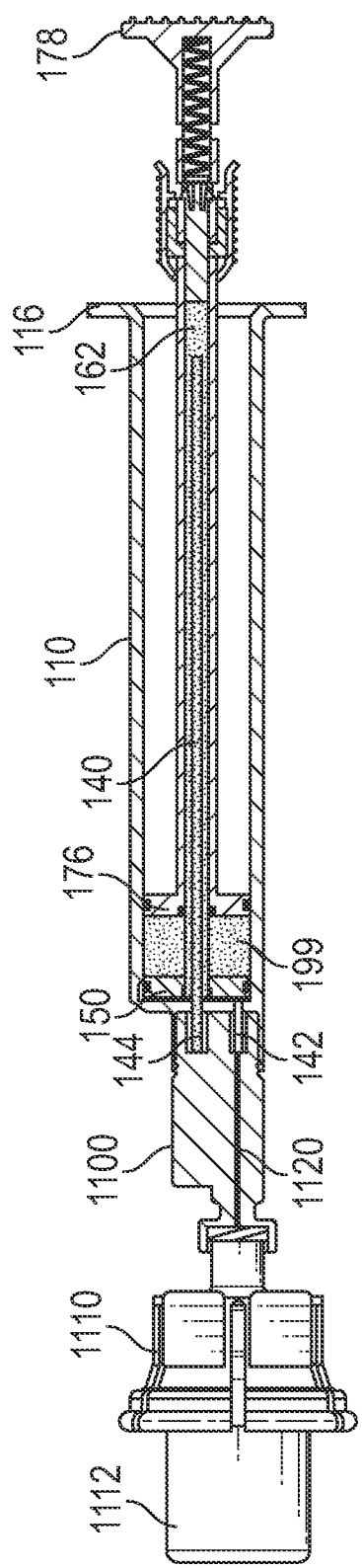
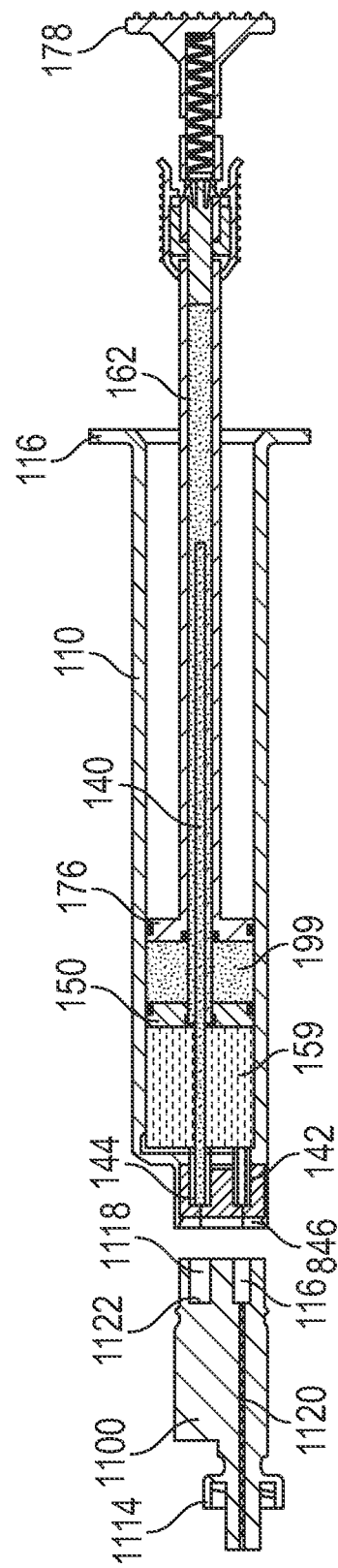
FIG. 17
FIG. 18

DUAL-CHAMBER SYRINGE WITH DUAL-LUMEN INTRAVENOUS SET

CROSS REFERENCE

This application is a continuation of U.S. application Ser. No. 16/598,945 filed Oct. 10, 2019 and claims priority from Provisional U.S. Application Ser. No. 62/744,500 filed on Oct. 11, 2018, and entitled DUAL-CHAMBER SYRINGE WITH DUAL-LUMEN INTRAVENOUS SET.

BACKGROUND

The delivery of medical fluids to fluid-restricted patients often includes administering the medical fluid intravenously through an intravenous (IV) set from a fluid source at low flow rates. Traditional practice often involves breaking the line to deliver an IV push, which can be time consuming at such low flow rates. Other conventional practices may involve administering a priming solution to the fluid-restricted patient via a pump before delivering the medical fluid, which may delay the medical fluid from being administered to the fluid-restricted patient in a timely fashion.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 8 illustrates a plan view of a dual-lumen intravenous (IV) set in accordance with aspects of the present disclosure.

FIG. 9 illustrates a plan view of the dual-lumen IV set of FIG. 8, with portions sectioned away and in phantom to depict interior details of the dual-lumen IV set in accordance with aspects of the present disclosure.

FIG. 17 illustrates a plan view of the dual-chamber syringe of FIG. 1, in a pre-filled state and in use with a vial, with portions sectioned and broken away to depict internal fluid passages, in accordance with aspects of the present disclosure.

FIG. 18 illustrates a plan view of the dual-chamber syringe of FIG. 17, in a post-filled state with the vial and the dual-chamber syringe adapter removed from the dual-chamber syringe, with portions sectioned and broken away to depict internal fluid passages, in accordance with aspects of the present disclosure.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

FIGS. 1-25 illustrate a fluid delivery system including a syringe-pump-compatible, dual-chamber syringe couplable to a dual-lumen intravenous (IV) set. The fluid delivery system is configured to remove priming solution from the dual-lumen IV set for reserve in the dual-chamber syringe, deliver medication at a pre-determined flow rate, and administer remaining medication residing in the dual-lumen IV set by restoring the reserved priming solution in the dual-chamber syringe to the dual-lumen IV set.

Figure 19:
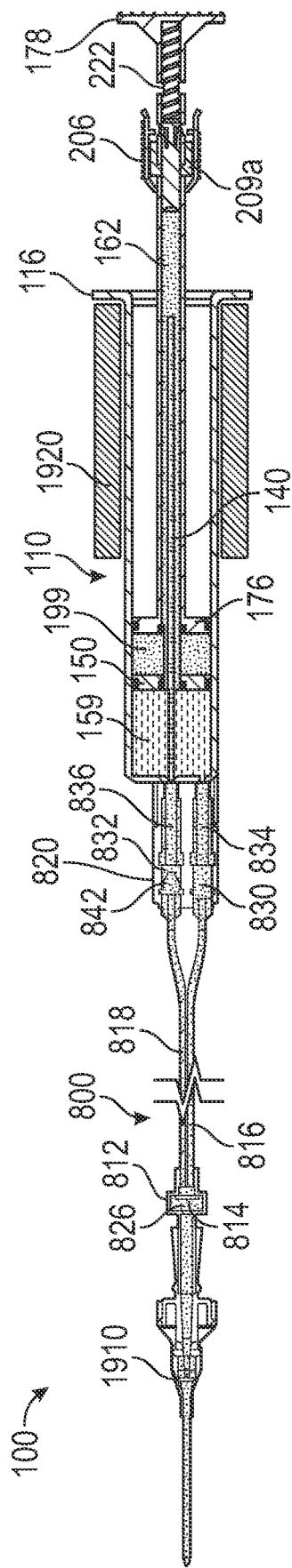
FIG. 19 illustrates a plan view of a fluid delivery system in a pre-priming of medication state, depicting the dual-chamber syringe of FIG. 1 in use with the dual-lumen IV set of FIG. 8, with portions sectioned and broken away to depict internal fluid passages, in accordance with aspects of the present disclosure.

FIGS. 1-6 illustrate an embodiment of a dual-chamber syringe 110 of a fluid delivery system 100 (shown in FIG. 19). In some embodiments, the dual-chamber syringe 110 includes a cylindrical syringe barrel 112, an end wall 114, and a syringe collar 116. The end wall 114 is disposed at a first end 118 of the syringe barrel 112 while the syringe collar 116 is disposed at a second end 120 of the syringe barrel 112, which is opposite the first end 118. The syringe collar 116 extends radially outwardly from the syringe barrel 112 proximate the second end 120. The syringe barrel 112 includes a cylindrical inner chamber 122 extending between the end wall 114 and the syringe collar 116.

Figure 1:
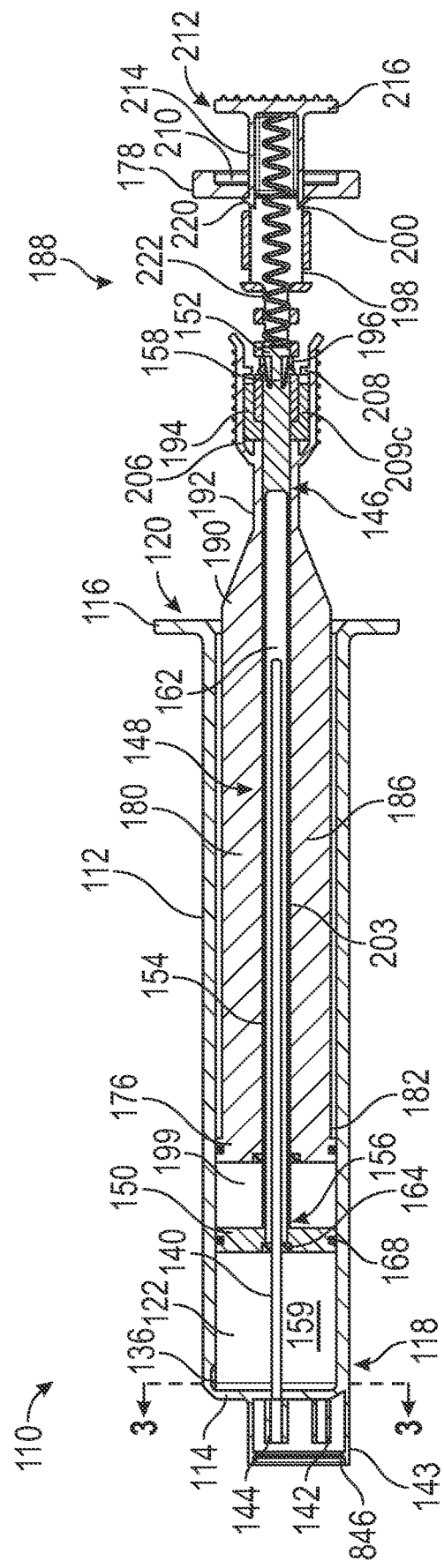
FIG. 1 illustrates a side view of a dual-chamber syringe, with portions sectioned and broken away to show details, in accordance with aspects of the present disclosure.
Figure 2:
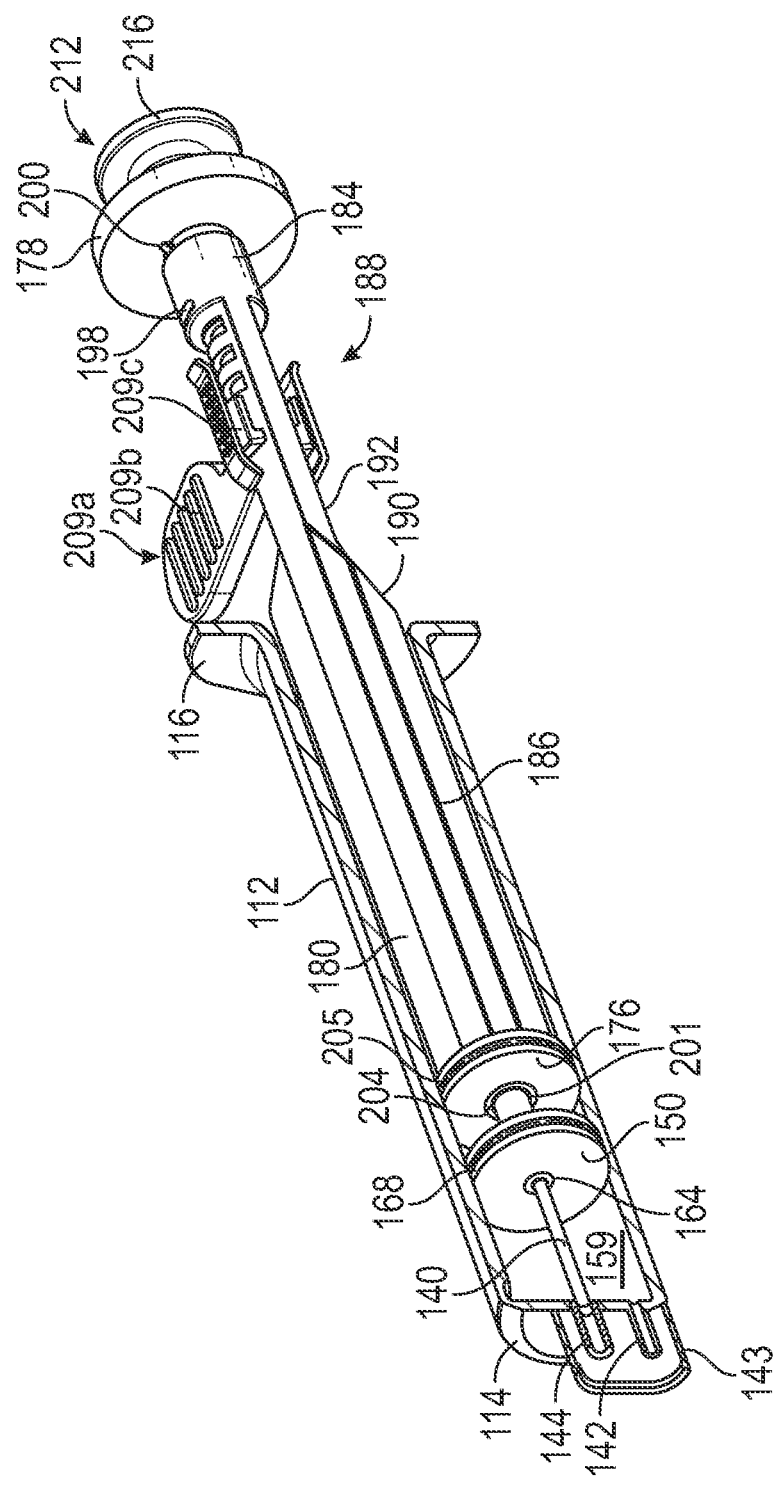
FIG. 2 illustrates a perspective view of the dual-chamber syringe depicted in FIG. 1 in accordance with aspects of the present disclosure.
Figure 3:
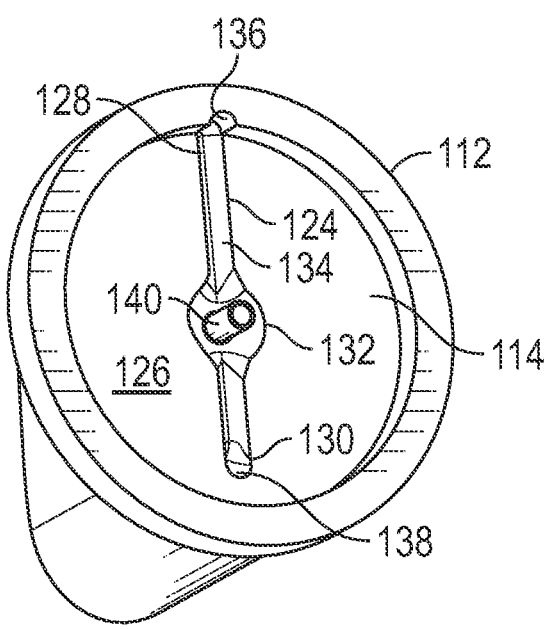
FIG. 3 illustrates a cross-sectional perspective view, taken along line 3-3 of the dual-chamber syringe of FIG. 1, depicting an end wall of the syringe in accordance with aspects of the present disclosure.
Figure 4:
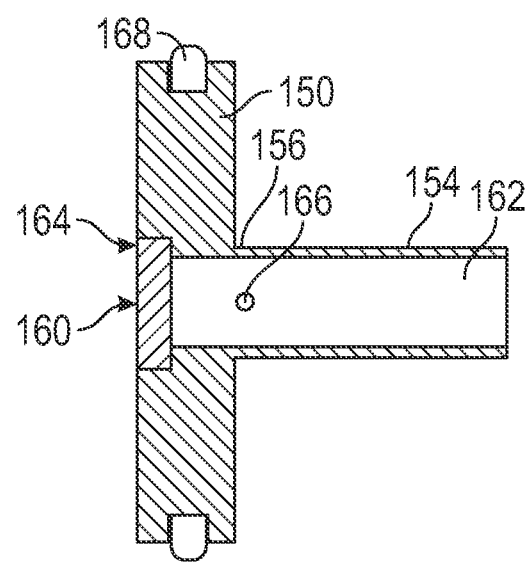
FIG. 4 illustrates a detailed cross-sectional view of a primary plunger of the dual-chamber syringe depicted in FIG. 1 in accordance with aspects of the present disclosure.
Figure 5:
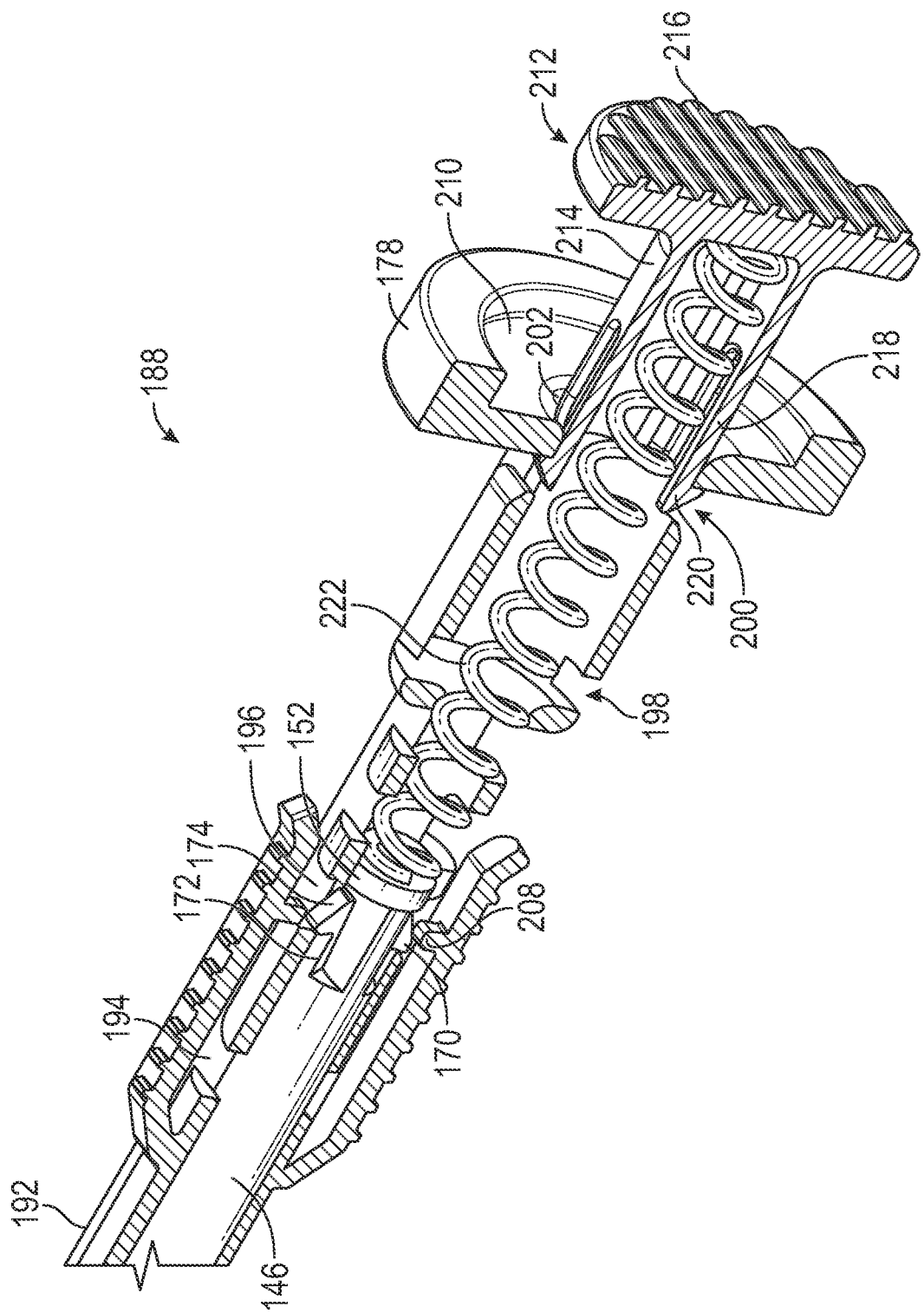
FIG. 5 illustrates a detailed cross-sectional perspective view of the dual-chamber syringe of FIG. 1 with an activator in an inactivated state in accordance with aspects of the present disclosure.

With particular reference to FIG. 3, a grooved channel 124 is recessed in an inner face 126 of the end wall 114. The inner face 126 faces the inner chamber 122 and is disposed therein. The channel 124 includes a notch end 128, a passage end 130, and a divot 132 disposed between the notch end 128 and the passage end 130. In some aspects, the channel 124 includes opposing beveled walls 134, which extend between the notch end 128 and the divot 132 and between the divot 132 and the passage end 130. The notch end 128 is in fluid communication with a notch 136, which is disposed in the syringe barrel 112 at an intersection of the syringe barrel 112 and the end wall 114 proximate the first end 118. The notch 136 extends axially inwardly from the end wall 114 within the inner chamber 122. The passage end 130 is in fluid communication with a passage 138 disposed through the end wall 114. In some aspects, the channel 124 extends along a portion of a diameter of the inner face 126. The notch 136, the channel 124, and the passage 138 collectively form a flushing fluid flow path of which the features and functionality will be described in more detail below.

The dual-chamber syringe 110 also includes an internal tube 140. The internal tube 140 is disposed through the divot 132 and the inner face 126 of the end wall 114 and extends axially inwardly within the inner chamber 122. The internal tube 140 terminates within the inner chamber 122 and is offset axially inwardly with respect to the syringe collar 116. In some aspects, the internal tube 140 extends substantially centrally through the divot 132 and the inner face 126 of the end wall 114 and is disposed centrally within the inner chamber 122.

The dual-chamber syringe 110 also includes a primary nozzle 142 and a secondary nozzle 144. Both the primary nozzle 142 and the secondary nozzle 144 extend axially outwardly from the end wall 114 and are disposed externally with respect to the inner chamber 122. In some aspects, the secondary nozzle 144 is disposed centrally on the end wall 114. The secondary nozzle 144 is coaxially aligned with the internal tube 140 and is in fluid communication with the internal tube 140. The primary nozzle 142 is radially offset on the end wall 114 from the secondary nozzle 144. The primary nozzle 142 is in fluid communication with a primary chamber 145 of the inner chamber 122 via the passage 138. A nozzle guide 143 also extends axially outwardly from the end wall 114 and surrounds both the primary nozzle 142 and the secondary nozzle 144 to facilitate connecting the dual-chamber syringe 110 to other medical components. In some aspects, the primary nozzle 142 and the secondary nozzle 144 are asymmetrical to prevent reversed or backwards coupling of the dual-chamber syringe 110 to the dual-lumen IV set (800). In some aspects, the primary nozzle 142 and the secondary nozzle 144 are male Luer connectors. In other aspects, the primary nozzle 142 is a male Luer connector and the secondary nozzle 144 is a needle-free connector. In yet other aspects, the primary nozzle 142 is a needle-free connector and the secondary nozzle 144 is a male Luer connector.

Moreover, the dual-chamber syringe 110 includes a primary plunger 146 and a secondary plunger 148. The primary plunger 146 is in mechanical association with the secondary plunger 148, such that both are received by the inner chamber 122 and are configured for slidable movement within the inner chamber 122. The primary plunger 146 includes a primary stopper 150, a primary head 152, and a rod 154 extending between the primary stopper 150 and the primary head 152. The primary stopper 150 is disposed at a first rod end 156 of the rod 154 and the primary head 152 is disposed at a second rod end 158 of the rod 154. The primary plunger 146 is arranged within the inner chamber 122, such that a primary chamber 159 is disposed between the primary stopper 150 and the inner face 126 of the end wall 114. The primary plunger 146 includes a primary receiving aperture 160 disposed centrally through the primary stopper 150. The rod 154 extends from the primary stopper 150 and includes a primary inner cavity 162, such that the primary inner cavity 162 is aligned with the primary receiving aperture 160. The primary receiving aperture 160 and the primary inner cavity 162 are configured to slidably receive the internal tube 140 of the dual-chamber syringe 110. In some aspects, a first primary O-ring 164 is disposed in the primary receiving aperture 160, such that the internal tube 140 is slidably and sealingly received by the first primary O-ring 164 and is slidably received by the primary inner cavity 162. A chamber passage 166 is disposed through the rod 154 proximate an intersection of the rod 154 and the primary stopper 150. In some aspects, a second primary O-ring 168 is disposed around the primary stopper 150 for sealing engagement with syringe barrel 112.

Figure 6:
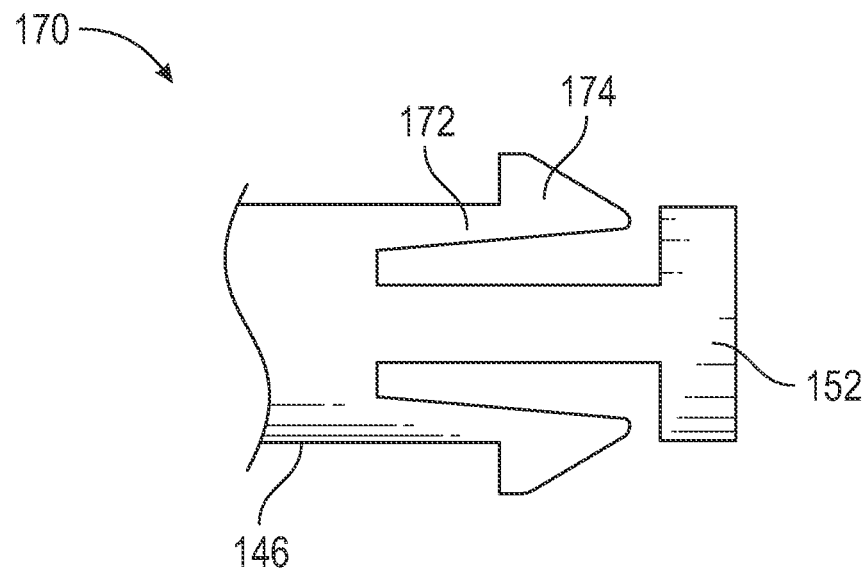
FIG. 6 illustrates a detailed plan view of a snap lock of the primary plunger depicted in FIG. 5 in accordance with aspects of the present disclosure.
Figure 7:
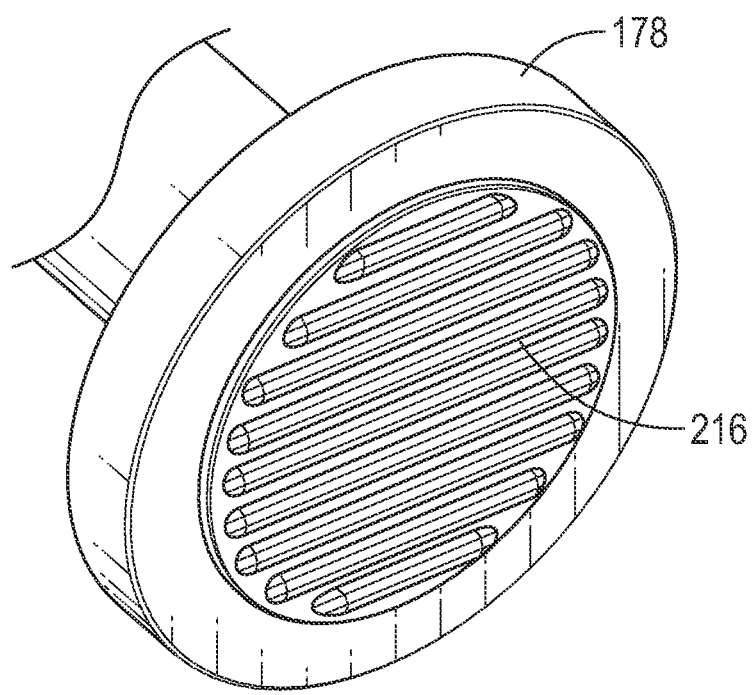
FIG. 7 illustrates a detailed perspective view of the activator depicted in FIG. 5, in an activated state, in accordance with aspects of the present disclosure.

The primary plunger 146 includes a lock member 170 disposed on the rod 154 between the primary inner cavity 162 and the primary head 152. With particular reference to FIG. 6, the lock member 170 includes opposed rod flanges 172. Each rod flange of the opposed rod flanges 172 includes a tapered tab 174, which protrudes radially outwardly and tapers axially towards the primary head 152. The opposed rod flanges 172 are depressible radially inwardly toward each other. The lock member 170 is mechanically associated with components of the secondary plunger 148 to releasably lock with the primary plunger 146, which will be described in more detail below.

The secondary plunger 148 includes a secondary stopper 176, a secondary head 178, and a body 180 extending between the secondary stopper 176 and the secondary head 178. The secondary stopper 176 is disposed at a first body end 182 of the body 180 and the secondary head 178 is disposed at a second body end 184 of the body 180. The body 180 includes a main section 186 and a neck section 188. In some aspects, the main section 186 of the body 180 includes wings including a plus-sign (e.g., +) cross-section. The main section 186 transitions to the neck section 188 at a tapered section 190. In some aspects, the neck section 188 includes a neck 192 disposed between the tapered section 190 and the secondary head 178. The neck 192 includes, sequentially in a direction from the tapered section 190 to the secondary head 178, first opposed plunger slots 194, second opposed plunger slots 196, opposed activator lock slots 198, and opposed activator rest slots 200. Moreover, the secondary plunger 148 includes a secondary receiving aperture 201 disposed centrally through the secondary stopper 176 and a head aperture 202 disposed centrally through the secondary head 178. The secondary plunger 148 includes a secondary inner cavity 203 extending from the secondary stopper 176 at the secondary receiving aperture 201 to the secondary head 178 at the head aperture 202. The secondary receiving aperture 201 and the secondary inner cavity 203 are configured to slidably receive the rod 154 of the primary plunger 146. In such an arrangement within the inner chamber 122, a secondary chamber 199 of the inner chamber 122 is disposed between the secondary stopper 176 and the primary stopper 150. In some aspects, a first secondary O-ring 204 is disposed in the secondary receiving aperture 201, such that the rod 154 is slidably and sealingly received by the first secondary O-ring 204 and is slidably received by the secondary inner cavity 203. In some aspects, a second secondary O-ring 205 is disposed around the secondary stopper 176 for sealing engagement with the syringe barrel 112.

Opposed lock flanges 206 protrude outwardly from the neck 192 and extend axially alongside the neck 192. A nub 208 protrudes radially inwardly from each lock flange of the opposed lock flanges 206. The nubs 208 are aligned with the second opposed plunger slots 196. The opposed lock flanges 206 are configured to urge radially inwardly toward each other, such that nubs 208 are received by the second opposed plunger slots 196. The opposed lock flanges 206 are deformable and configured to be urged radially outwardly away from each other when engaged with a pin 209a. For example, the pin 209a includes a pull tab 209b formed to a clasp 209c, such that the clasp 209c is removably fastened around the neck 192 and arranged between the opposed lock flanges 206 and the neck 192 to urge the opposed lock flanges 206 radially outwardly. With the opposed lock flanges 206 urged radially outwardly away from each other, the nubs 208 are held radially outwardly away from the second opposed plunger slots 196.

The secondary plunger 148 includes a seat 210 centrally recessed into the secondary head 178 and aligned coaxially with the secondary inner cavity 203 and the head aperture 202. The secondary plunger 148 also includes an activator 212. The activator 212 includes an activator body 214 and an activator head 216, which sits on the activator body 214. The activator body 214 is substantially cylindrical and includes opposed activator flanges 218 formed in the activator body 214. Each activator flange of the opposed activator flanges 218 includes a tapered tab 220, which protrudes radially outwardly and tapers axially inwardly. The opposed activator flanges 218 are depressible radially inwardly toward each other. The activator body 214 is received by the head aperture 202, such that, in the inactivated state of the activator 212, the tapered tabs 220 of the opposed activator flanges 218 are received by the opposed activator rest slots 200 and, in an activated state of the activator 212, the tapered tabs 220 are received by, and seated at, the opposed activator lock slots 198 while the activator head 216 is received by the seat 210. Moreover, when the dual-chambered syringe 110 is assembled, a resilient member 222 is disposed within the neck 192 between the activator head 216 and the primary head 152 of the primary plunger 146. The resilient member 222 is in an uncompressed state when the activator 212 is in the inactivated state and is in a compressed state when the activator 212 is in the activated state.

Figure 10:
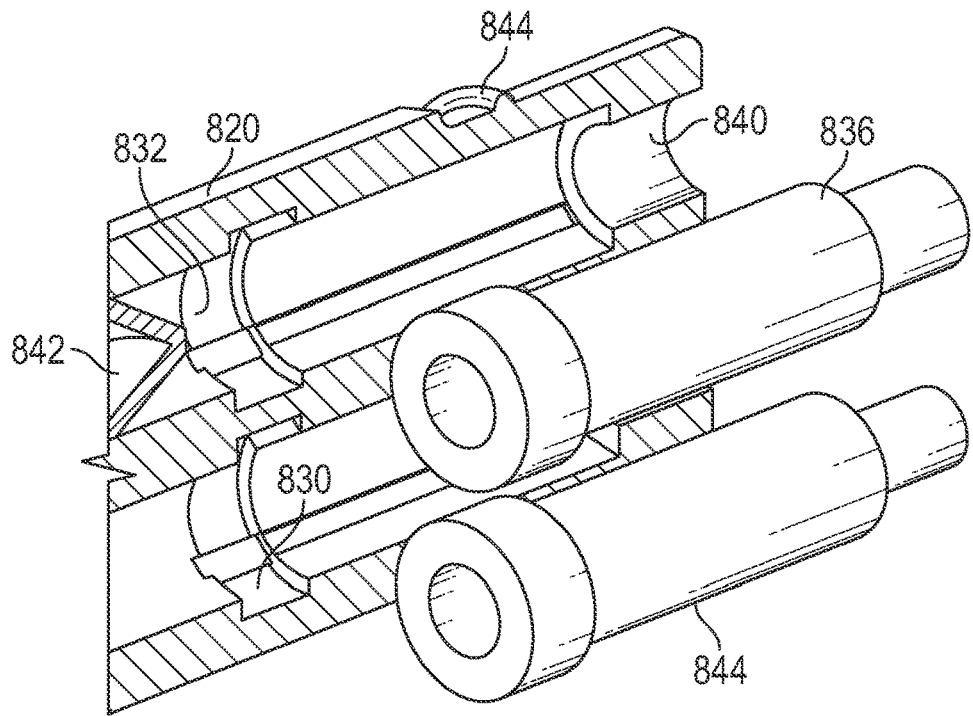
FIG. 10 illustrates a detailed perspective view of a dual-lumen tube adapter of the dual-lumen IV set of FIG. 9 in accordance with aspects of the present disclosure.

With reference to FIGS. 8-10, the fluid delivery system 100 also includes a dual-lumen intravenous (IV) set 800, which is couplable to the dual-chamber syringe 110. Although the dual-lumen IV set 800 is illustrated with broken lines depicting a shortened length, it should be understood that the length of the dual-lumen IV set 800 can be any length including, but not limited to, 1 meter, 2 meters, 3 meters, etc. The dual-lumen IV set 800 includes a connector 810, a valve housing 812, a valve 814, a primary lumen 816, a secondary lumen 818, and an adapter 820. The connector 810 includes an exit port 822 and a channel 824 fluidly connected to the exit port 822. The connector 810 is configured to couple with a medical device, such as, for example, a catheter (now shown). Although the fluid delivery system 100 is illustrated with one dual-lumen IV set 800, it is within the scope of the present application that the fluid delivery system 100 includes multiple dual-lumen IV sets to deliver multiple drugs via multiple dual-chamber syringes in one IV set. The channel 824 is also fluidly connected to a housing passage 826 disposed in the valve housing 812. In some aspects, the channel 824 tapers from the housing passage 826 toward the exit port 822. A housing port 828 is also disposed in the valve housing 812 and is in fluid communication with the housing passage 826. An end of each of the primary lumen 816 and the secondary lumen 818 are received by, and in fluid communication with, the housing port 828. The other end of the primary lumen 816 is in fluid communication with a primary duct 830 disposed in the adapter 820 while the other end of the secondary lumen 818 is in fluid communication with a secondary duct 832 also disposed in the adapter 820, which is offset from the primary duct 830.

The valve 814 is disposed in the valve housing 812 and is configured to seal the housing port 828 from the housing passage 826 until a predetermined cracking pressure is achieved against the valve 814 from the housing port 828 at which point fluid is allowed to flow from the housing port 828 past the valve 814 and to the housing passage 826. In some aspects, the valve 814 is a one-way valve, such as, but not limited to, a check valve or an anti-siphon valve. The predetermined cracking pressure can be selected to crack at any predetermine pressure, such as, for example, 1 psi (pounds per square inch) or a half psi.

The adapter 820 also includes a primary septum 834 and a secondary septum 836. The primary septum 834 is disposed in the primary duct 830. The primary septum 834 is configured to seal a primary port 838 of the adapter 820, which is disposed at an end of the primary duct 830, to prevent fluid flow from the primary port 838 to the primary duct 830 when unengaged with a medical device. When the adapter 820 is coupled to the dual-chamber syringe 110, however, the primary nozzle 142 engages the primary septum 834 allowing fluid from the primary nozzle 142 to flow through the primary port 838 to the primary lumen 816 via the primary duct 830. The secondary septum 836 is disposed in the secondary duct 832 and is configured to seal a secondary port 840 of the adapter 820, which is disposed at an end of the secondary duct 832, to prevent fluid flow from the secondary duct 832 to the secondary port 840 when unengaged with a medical device. When the adapter 820 is coupled to the dual-chamber syringe 110, however, the secondary nozzle 144 engages the secondary septum 836 allowing fluid from the secondary duct 832 to flow through the secondary port 840 to the secondary nozzle 144. Moreover, a secondary valve 842 is disposed in the secondary duct 832 to allow fluid flow from the secondary lumen 818 to the secondary nozzle 144 via the secondary duct 832, but prevents fluid flow in the opposite direction from the secondary nozzle 144 to secondary lumen 818. In some aspects, the secondary valve 842 is a one-way valve, such as, but not limited to a duckbill valve or a check valve. Because in some aspects the primary nozzle 142 and the secondary nozzle 144 are asymmetrical, the primary nozzle 142 is configured to be received only by the primary port 838 and cannot be received by the secondary port 840 while the secondary nozzle 144 is configured to be received only by the secondary port 840 and cannot be received by the primary port 838 to prevent reversed or backwards coupling of the dual-chamber syringe 110 to the dual-lumen IV set 800.

The adapter 820 also includes a ridge 844 disposed around the exterior and axially offset inwardly from the primary port 838 and the secondary port 840. The ridge 844 is configured to removably snap fit or interlock with a seat 846 disposed on the interior of the nozzle guide 143 when the dual-chamber syringe 110 and the dual-lumen IV set 800 are coupled together. In some aspects, a first plurality of serrations 848 is disposed on the exterior of the adapter 820 to facilitate gripping when being hand-held.

Figure 11:
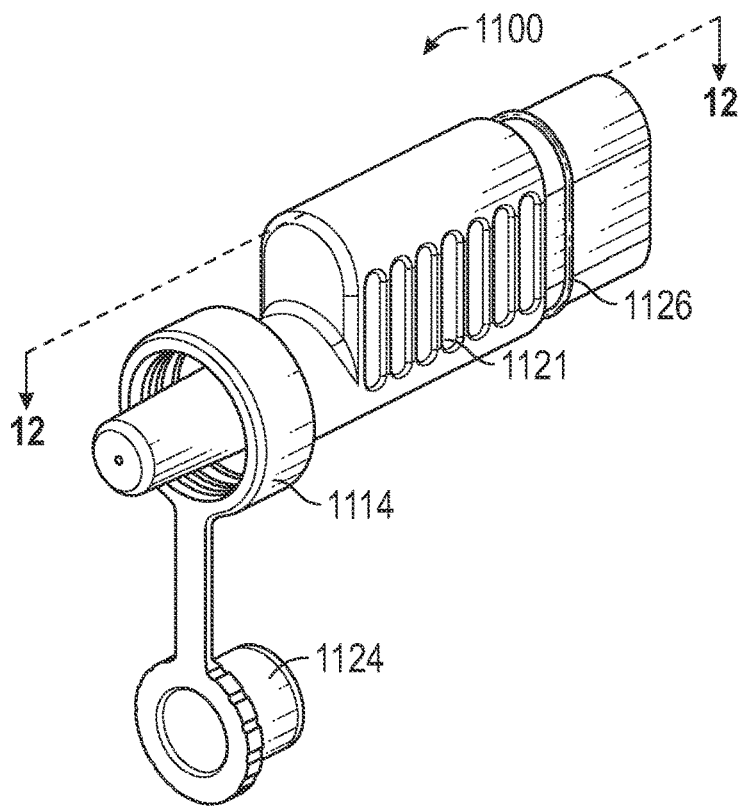
FIG. 11 illustrates a perspective view of a dual-chamber syringe adapter in accordance with aspects of the present disclosure.
Figure 12:
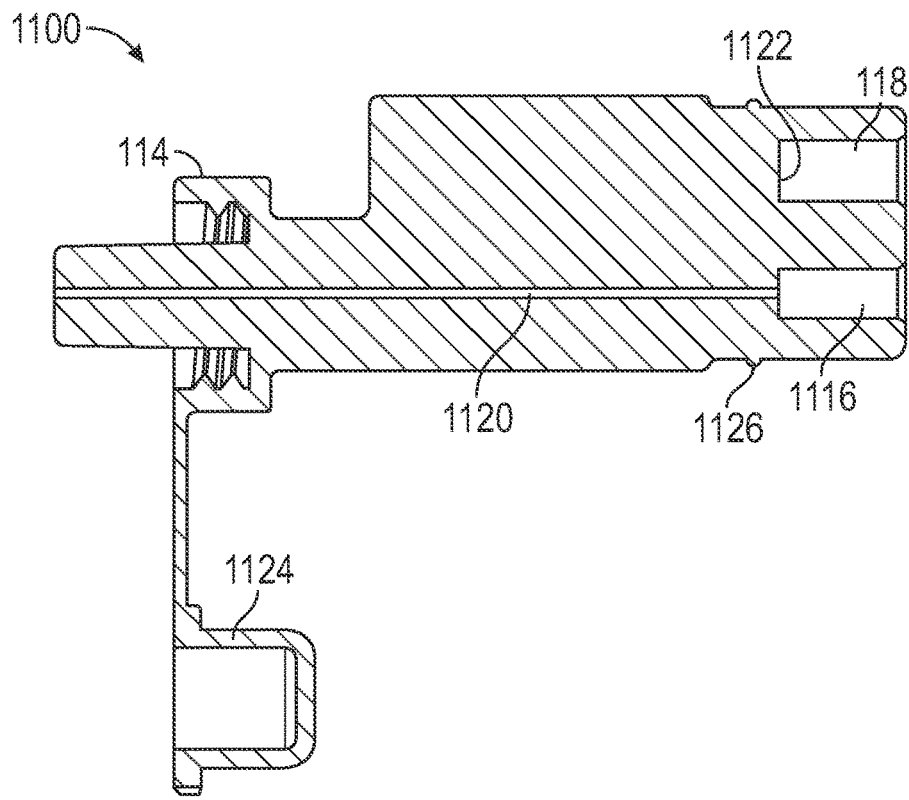
FIG. 12 illustrates a cross-sectional plan view taken along line 12-12 of FIG. 11 in accordance with aspects of the present disclosure.

With reference to FIGS. 11-12, the fluid delivery system 100 also includes a dual-chamber syringe adapter 1100. The dual-chamber syringe adapter 1100 is couplable to the dual-chamber syringe 110 and a vial adapter 1110 (shown in FIG. 17), which is in turn coupled to a vial 1112 (also shown in FIG. 17). The dual-chamber syringe adapter 1100 is configured to transfer fluid in the vial 1112 to the dual-chamber syringe 110. The dual-chamber syringe adapter 1100 includes a male connector 1114, a primary nozzle receiver 1116, a secondary nozzle receiver 1118, and a conduit 1120. In some aspects, a second plurality of serrations 1121 is disposed on the exterior of the dual-chamber syringe adapter 1100 to facilitate gripping when being hand-held. The conduit 1120 is disposed through the dual-chamber syringe adapter 1100 and fluidly couples the male connector 1114 to the primary nozzle receiver 1116. A nozzle seat 1122 is disposed in the secondary nozzle receiver 1118 for sealing engagement with the secondary nozzle 144 and preventing any fluid flow through the secondary nozzle 144. The dual-chamber syringe adapter 1100 also includes a cap 1124 hingedly coupled to the male connector 1114 for removably capping or closing the male connector 1114. In some aspects, the male connector 1114 is a male Luer connector. The male connector 1114 is configured to couple with a female connector of the vial adapter 1110. The primary nozzle receiver 1116 is configured to matingly receive the primary nozzle 142 of the dual-chamber syringe 110 and the secondary nozzle receiver 1118 is configured to matingly receive the secondary nozzle 144 of the dual-chamber syringe 110 while an adapter ridge 1126 disposed on the exterior of the dual-chamber syringe adapter 1100 removably snap fits or interlocks with the seat 846. When the dual-chamber syringe adapter 1100 is coupled to the dual-chamber syringe 110 fluid in the vial 1112 is capable of being drawn into the primary chamber 159 through the primary nozzle 142 via the vial adapter 1110, the male connector 1114, and the conduit 1120.

Figure 13:
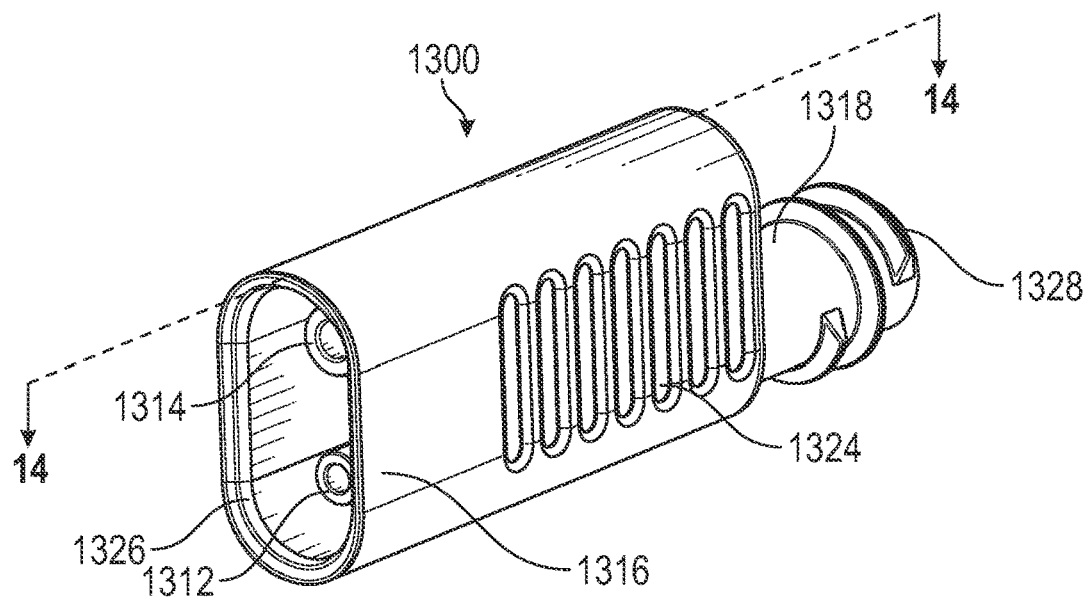
FIG. 13 illustrates a perspective view of a flush syringe adapter in accordance with aspects of the present disclosure.
Figure 14:
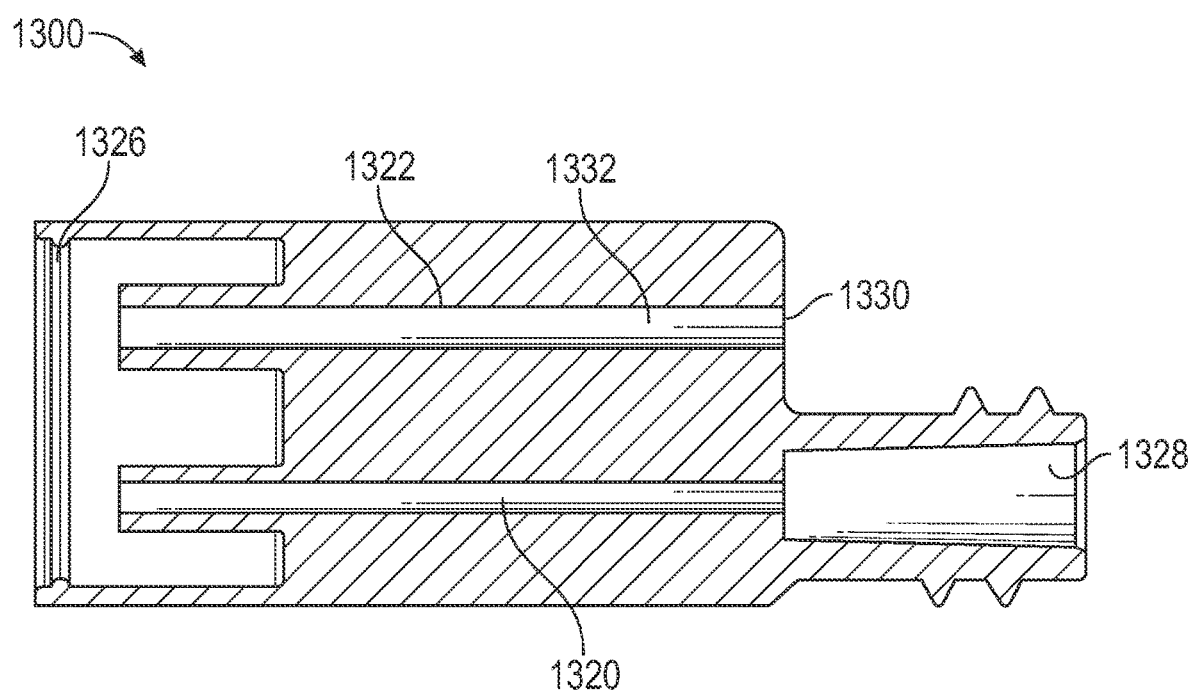
FIG. 14 illustrates a cross-sectional plan view taken along line 14-14 of FIG. 13 in accordance with aspects of the present disclosure.

With reference to FIGS. 13 and 14, the fluid delivery system 100 also includes a flush syringe adapter 1300. The flush syringe adapter 1300 is couplable to a flush syringe 1310 (shown in FIG. 15) and the adapter 820 of the dual-lumen IV set 800. The flush syringe adapter 1300 is configured to transfer fluid from the flush syringe 1310 to prime the dual-lumen IV set 800 with saline. The flush syringe adapter 1300 includes a primary adapter nozzle 1312, a secondary adapter nozzle 1314, a syringe guide 1316, a female connector 1318, a primary passage 1320, and a secondary passage 1322. In some aspects, a third plurality of serrations 1324 is disposed on the exterior of the flush syringe adapter 1300 to facilitate gripping when being hand-held. The syringe guide 1316 surrounds the primary adapter nozzle 1312 and the secondary adapter nozzle 1314 to facilitate coupling the flush syringe adapter 1300 to the dual-lumen IV set 800 so that the primary adapter nozzle 1312 is received by the primary port 838 of the adapter 820 and the secondary adapter nozzle 1314 is received by the secondary port 840. In some aspects, the primary adapter nozzle 1312 and the secondary adapter nozzle 1314 are asymmetrical, such that the primary adapter nozzle 1312 is configured to be received only by the primary port 838 and cannot be received by the secondary port 840 while the secondary adapter nozzle 1314 is configured to be received only by the secondary port 840 and cannot be received by the primary port 838 to prevent reversed or backwards coupling of the flush syringe adapter 1300 to the dual-lumen IV set 800. In some aspects, the primary adapter nozzle 1312 and the secondary adapter nozzle 1314 are male Luer connectors. In other aspects, the primary adapter nozzle 1312 is a male Luer connector and the secondary adapter nozzle 1314 is a needle-free connector. In yet other aspects, the primary adapter nozzle 1312 is a needle-free connector and the secondary adapter nozzle 1314 is a male Luer connector.

The primary passage 1320 is disposed between, and fluidly couples, the primary adapter nozzle 1312 and an adapter port 1328 disposed at the female connector 1318. In some aspects, the female connector 1318 is a female Luer connector. The female connector 1318 is configured to couple with a male connector of the flush syringe 1310. In some aspects, the male connector of the flush syringe 1310 is a male Luer connector. The secondary passage 1322 is disposed between, and fluidly couples, the secondary adapter nozzle 1314 and a vent 1330. A hydrophobic element 1332 is disposed in the secondary passage 1322 and is configured to allow air from the secondary adapter nozzle 1314 to escape through the vent 1330, but when the hydrophobic element 1332 contacts liquid fluid (e.g., saline from the flush syringe 1310) it prevents the liquid fluid from flowing out of the vent 1330.

Figure 15:
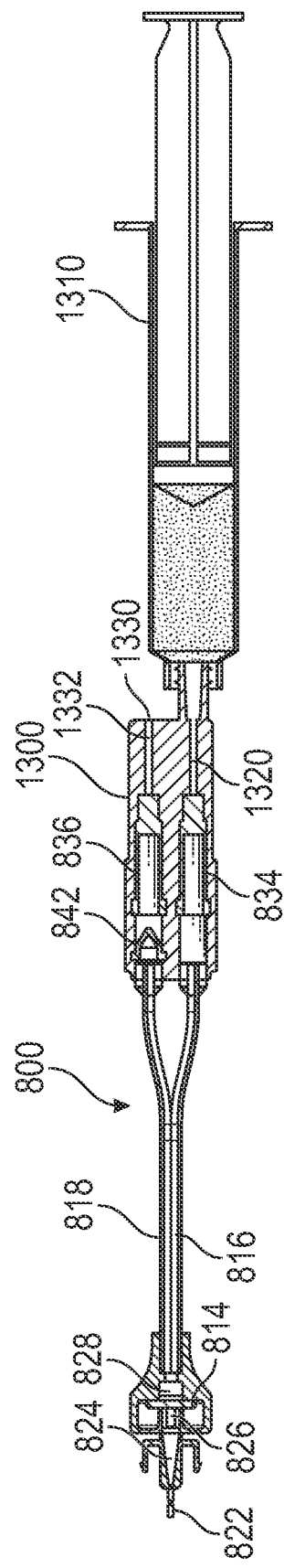
FIG. 15 illustrates a plan view of the dual-lumen IV set in use with a flush syringe in a pre-priming state, with portions sectioned and broken away to depict internal fluid passages, in accordance with aspects of the present disclosure.
Figure 16:
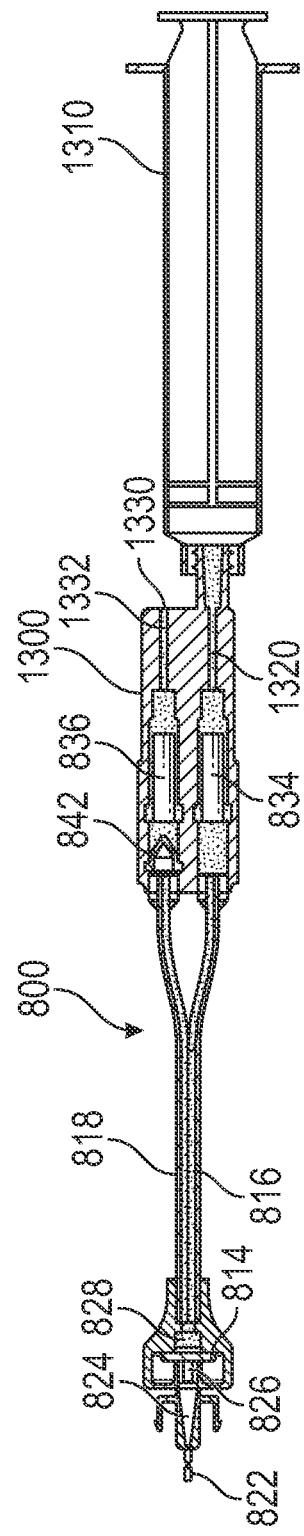
FIG. 16 illustrates a plan view of the dual-lumen IV set in use with the flush syringe of FIG. 15 in a post-priming state, with portions sectioned and broken away to depict internal fluid passages, in accordance with aspects of the present disclosure.

FIG. 15 illustrates the dual-lumen IV set 800 in use with the flush syringe 1310 in a pre-priming state and FIG. 16 illustrates the dual-lumen IV set 800 in use with the flush syringe 1310 in a post-priming state. In order to prime the dual-lumen IV set 800, which may occur at a patient bedside, the flush syringe adapter 1300 is coupled to the dual-lumen IV set 800, such that the primary adapter nozzle 1312 and the secondary adapter nozzle 1314 are received by the primary port 838 and the secondary port 840, respectively, and the adapter seat 1326 removably snap fits with the ridge 844 of the adapter 820. With the flush syringe adapter 1300 coupled to the dual-lumen IV set 800, the dual-chamber syringe adapter 1100, which is pre-filled with saline, is coupled to the flush syringe adapter 1300 via the female connector 1318. The flush syringe 1310 delivers the saline through the adapter port 1328 and the primary passage 1320 into the primary port 838 and the primary duct 830. The saline flows from the primary duct 830 through the primary lumen 816 until it reaches the housing port 828 and the valve 814. The pressure against the valve 814 is less than the predetermined cracking pressure so the saline travels through the secondary lumen 818 and the secondary valve 842. During this flow process, air in the dual-lumen IV set 800 has been pushed through the hydrophobic element 1332 and out the vent 1330, but once the saline contacts the hydrophobic element 1332, it prevents the saline from flowing any further. As the saline is prevented from flowing past the hydrophobic element 1332, the rest of the dual-lumen IV set 800 is primed with the saline. After the dual-lumen IV set 800 is fully primed, it can then be coupled to a medical device, such as a catheter. With the dual-lumen IV set 800 coupled to the catheter, the rest of the saline in the flush syringe 1310 is flushed through creating a pressure against the valve 814, because the hydrophobic element 1332 is preventing saline flow, that is higher than the predetermined cracking pressure, such that the valve 814 allows the saline to flow past to the housing passage 826 and out the exit port 822 to the catheter. The flush syringe adapter 1300, along with the flush syringe 1310, is then uncoupled from the dual-lumen IV set 800.

FIG. 17 illustrates the dual-chamber syringe 110 in a pre-filled state and in use with the vial 1112 and FIG. 18 illustrates the dual-chamber syringe 110, in a post-filled state with the vial 1112 and the dual-chamber syringe adapter 1100 uncoupled from the dual-chamber syringe 110. The pin 209*a* is inserted around the neck 192 urging the opposed lock flanges 206 radially outwardly, such that the nubs 208 are held radially outwardly away from the second opposed plunger slots 196. With the nubs 208 arranged in this manner, the tapered tabs 174 of the lock member 170 are removably received at the second opposed plunger slots 196 locking the primary plunger 146 to the secondary plunger 148. With the activator 212 in the inactivated state, the tapered tabs 220 of the opposed activator flanges 218 are received by and seated at the opposed activator rest slots 200, such that the resilient member 222 is in its uncompressed state between the primary head 152 of the primary plunger 146 and the activator head 216. This arrangement locks the primary plunger 146 to the secondary plunger 148 so that the primary stopper 150 is offset from the secondary stopper 176 at a predetermined distance, which can be preselected according to specific desires of a pre-filled volume of the secondary chamber 199. The dual-chamber syringe 110 is pre-filled with saline in the secondary chamber 199, as illustrated in FIG. 17.

In use, such as at a pharmacy environment, the activator 212 of the dual-chamber syringe 110 is activated by compressing the activator head 216 axially inward, such that the tapered tabs 220 of the opposed activator flanges 218 are depressed radially towards each other, unseated from the opposed activator rest slots 200, and received by the opposed activator lock slots 198 in locking fashion while the activator head 216 is received by the seat 210. In this arrangement, the resilient member 222 is in its compressed state between the primary head 152 of the primary plunger 146 and the activator head 216 positioned at the seat 210. Allowing the resilient member 222 to be in the uncompressed state before use can extend the shelf life of the dual-chamber syringe 110. After activating the activator 212, the dual-chamber syringe 110 is coupled to the dual-chamber syringe adapter 1100, such that the nozzle guide 143 facilitates the primary nozzle 142 being matingly inserted into the primary nozzle receiver 1116 and the secondary nozzle 144 being matingly inserted into the secondary nozzle receiver 1118 while the adapter ridge 1126 removably snap fits or interlocks with the seat 846. With the secondary nozzle 144 received by the secondary nozzle receiver 1118 and seated against the nozzle seat 1122, the saline is prevented from accidentally flowing out of the secondary chamber 199 during fluid transfer from the vial 1112 to the dual-chamber syringe 110.

With the dual-chamber syringe adapter 1100 coupled to the dual-chamber syringe 110, the male connector 1114 is coupled to the vial adapter 1110, which is coupled to the vial 1112. As the primary plunger 146 is locked to the secondary plunger 148, pulling the secondary head 178 axially away from the syringe collar 116 will draw the fluid in the vial 1112 (e.g., medicine) through the dual-chamber syringe adapter 1100 and the primary nozzle 142 and into the primary chamber 159 via the passage 138, and without disturbing the saline in the secondary chamber 199, the internal tube 140, and the primary inner cavity 162. Once the desired amount of medicine is drawn into the primary chamber 159 the dual-chamber syringe adapter 1100 can be uncoupled from the dual-chamber syringe 110, as depicted in FIG. 18.

FIG. 19 illustrates the dual-chamber syringe 110 of the fluid delivery system 100 in a pre-priming of medication state and in use with the dual-lumen IV set 800. The dual-lumen IV set 800 is primed with saline and is fluidly coupled to a catheter 1910. The dual-lumen IV set 800 is also fluidly coupled to the dual-chamber syringe 110, which is in mechanical engagement with a syringe pump 1920. While the syringe pump 1920 securely supports the syringe barrel 112, the syringe pump 1920 is also in mechanical engagement with the secondary head 178 to selectively control axially movement of the secondary plunger 148.

Figure 20:
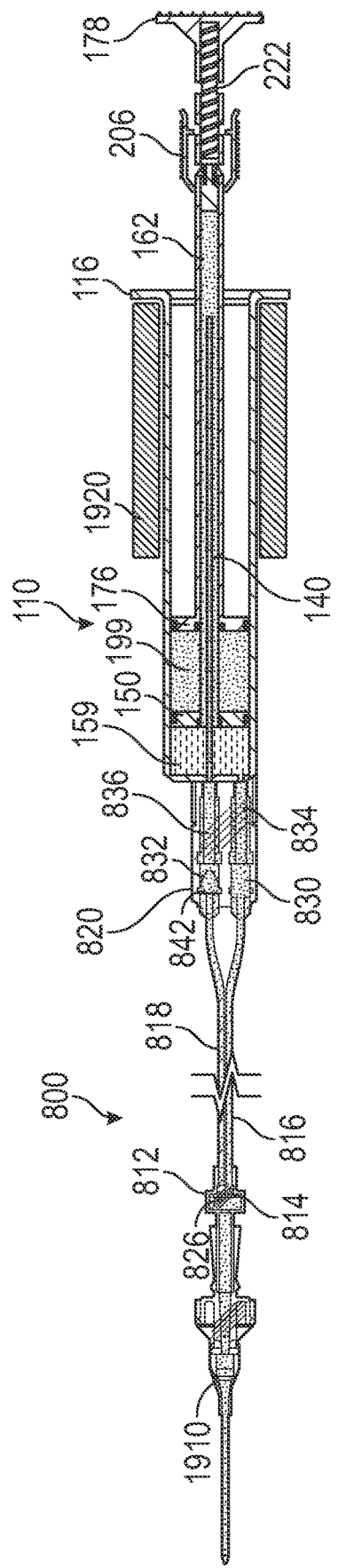
FIG. 20 illustrates a plan view of the fluid delivery system of FIG. 19 in a post-priming of medication state, depicting the dual-lumen IV set primed with medication, with portions sectioned and broken away to depict internal fluid passages, in accordance with aspects of the present disclosure.

From the pre-priming of medication state, the dual-chamber syringe 110 and dual-lumen IV set 800 transition to a post-priming of medication state, as illustrated in FIG. 20. The transition involves removing the pin 209*a* from the neck 192, such that the opposed lock flanges 206 are urged radially towards each other and the nubs 208 engage the tapered tabs 174 of the lock member 170 releasing the tapered tabs 174 from the second opposed plunger slots 196. With the secondary head 178 held in place by the syringe pump 1920, the release or unseating of the tapered tabs 174 from the second opposed plunger slots 196 allows the resilient member 222, in the compressed state, to urge against the primary head 152, which in turn urges the primary plunger 146 axially toward the end wall 114. As the primary plunger 146 is urged axially toward the end wall 114, the medication in the primary chamber 159 is forced through the passage 138 and out the primary nozzle 142 into the primary duct 830 to the primary lumen 816. At the same time, and because the pressure against the valve 814 is less than the predetermined cracking pressure, the medication is displacing the saline that was primed in the dual-lumen IV set 800 to travel out the secondary port 840 and through the secondary nozzle 144 to fill the secondary chamber 199 via the internal tube 140, the primary inner cavity 162, and the chamber passage 166. The primary plunger 146 continues to prime the dual-lumen IV set 800 with the medication until the tapered tabs 174 are received by, and seated against, the first opposed plunger slots 194, which prevents the resilient member 222 from urging the primary plunger 146 any further.

Figure 21:
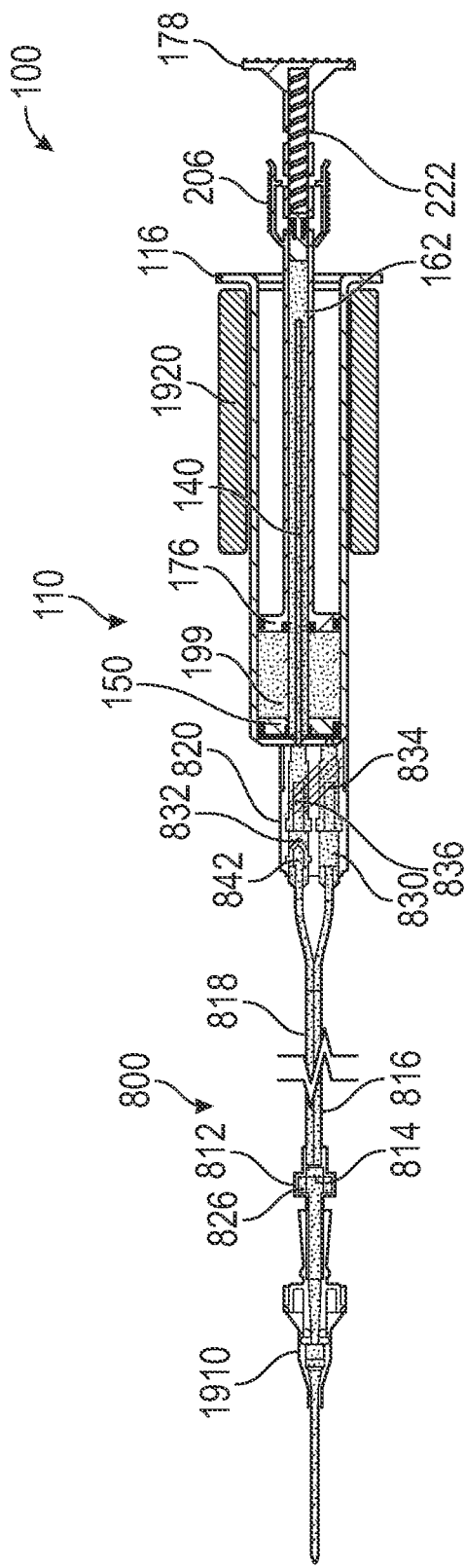
FIG. 21 illustrates a plan view of the fluid delivery system of FIG. 19 in a pre-flushing state, with portions sectioned and broken away to depict internal fluid passages, in accordance with aspects of the present disclosure.

From the post-priming of medication state, the dual-chamber syringe 110 and dual-lumen IV set 800 transition to a pre-flushing state, as illustrated in FIG. 21. The transition involves the syringe pump 1920 moving the secondary head 178 of the secondary plunger 148 axially toward the end wall 114 to deliver the remaining medication in the primary chamber 159 through the passage 138 and the primary nozzle 142 to the primary duct 830 and the primary lumen 816. Because the secondary valve 842 prevents saline flow from the secondary chamber 199 to the secondary lumen 818, pressure is increased against the valve 814 as the secondary plunger 148 is moved axially and is greater than the predetermined cracking pressure, such that the axially movement of the secondary plunger 148 forces the medication past the valve 814 and into the housing passage 826 to the catheter 1910 via the channel 824 and the exit port 822. As the secondary plunger 148 is being moved axially toward the end wall 114, the tapered tabs 174 are unseated from the first opposed plunger slots 194 and are moved towards the second opposed plunger slots 196.

Figure 22:
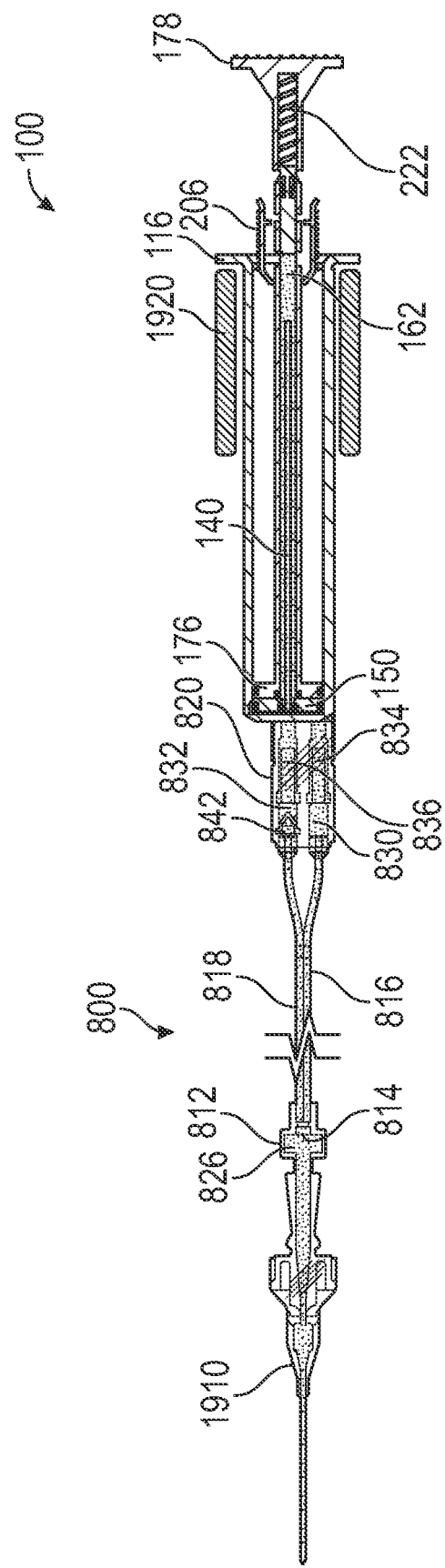
FIG. 22 illustrates a plan view of the fluid delivery system of FIG. 19 in a post-flushing state, with portions sectioned and broken away to depict internal fluid passages, in accordance with aspects of the present disclosure.
Figure 23:
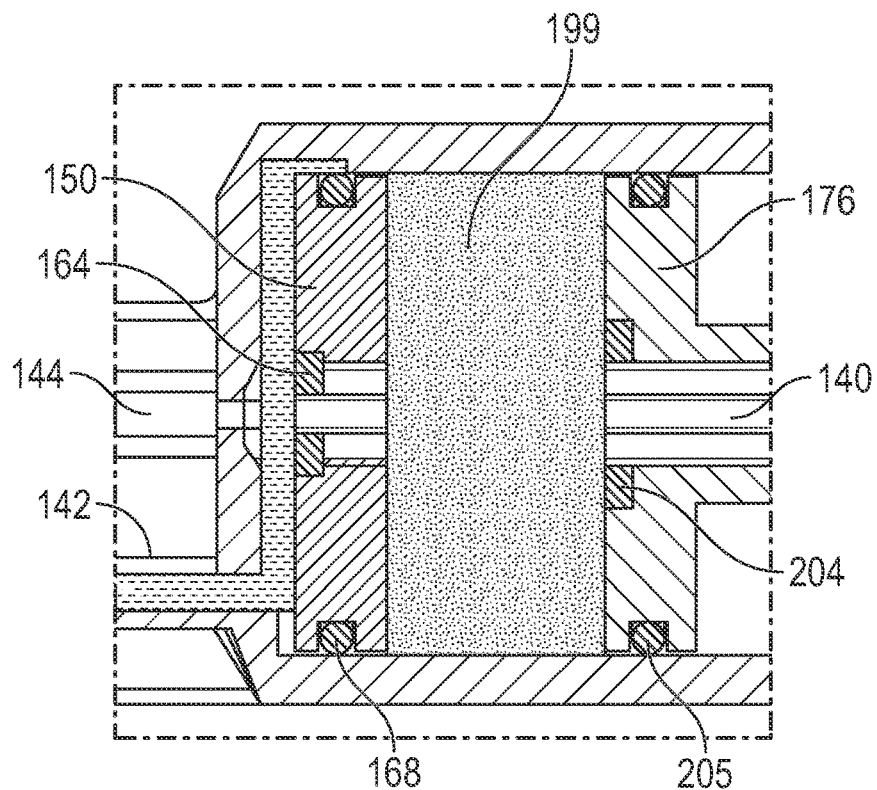
FIGS. 23-26 illustrates detailed views of the dual-chamber syringe transitioning from the pre-flushing state depicted in FIG. 21 to the post-flushing state depicted in FIG. 22.
Figure 24:
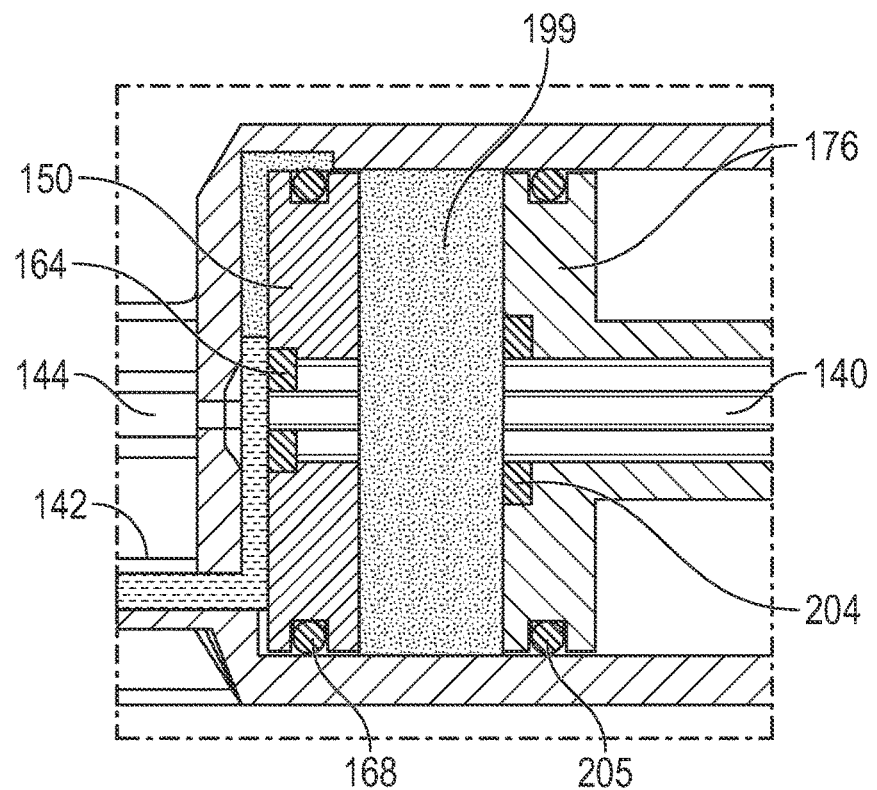
Figure 25:
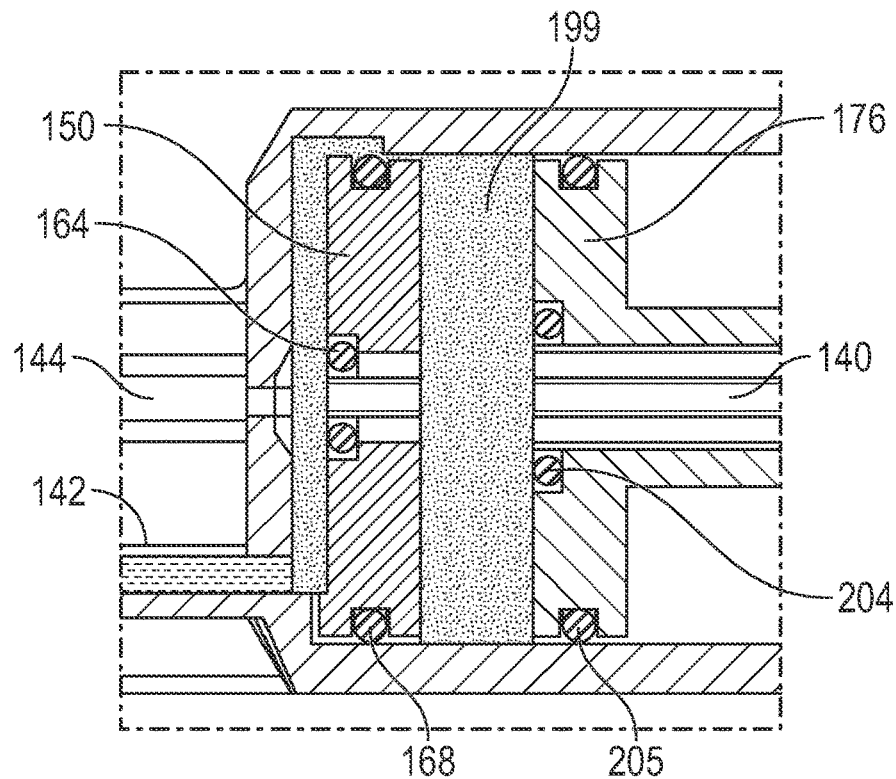
Figure 26:
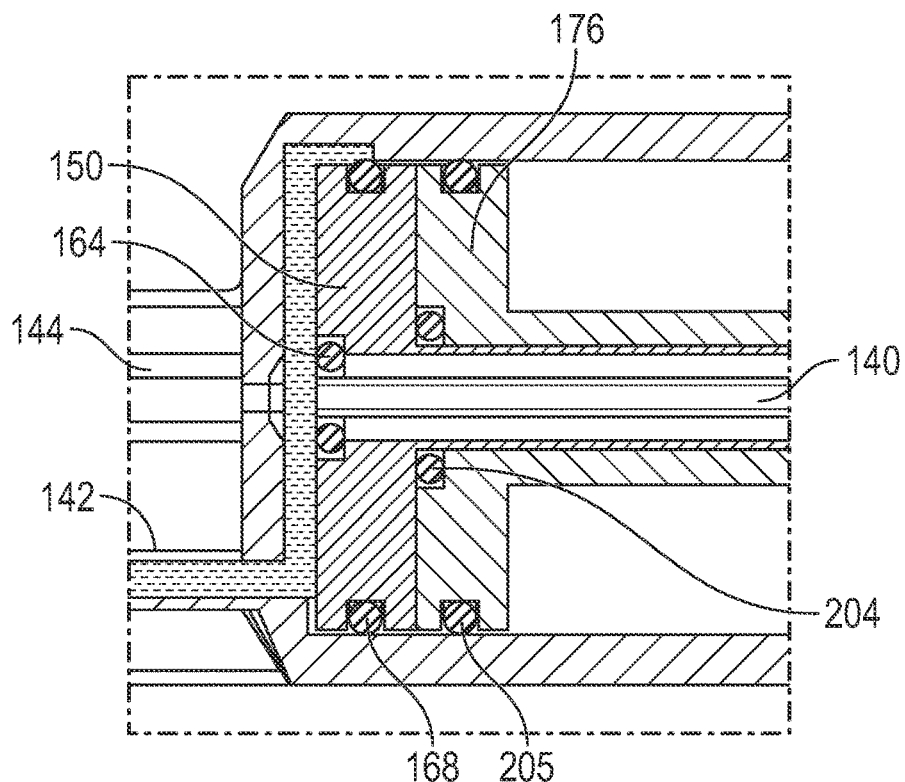

Once the primary stopper 150 abuts the inner face 126 of the end wall 114, the dual-chamber syringe 110 and dual-lumen IV set 800 transitions from the pre-flushing state to a post-flushing state, as illustrated in FIG. 22. The transition is illustrated in FIGS. 23-26. FIG. 23 illustrates the pre-flushing state with the primary stopper 150 abutting the inner face 126 of the end wall 114 and medication residing in the channel 124 and the notch 136. The second primary O-ring 168 seals the notch 136 and prevents the medication from flowing into the secondary chamber 199. As the secondary plunger 148 is continued to be moved axially toward the end wall 114 during the transition, the pressure against the second primary O-ring 168 increases, such that the saline in the secondary chamber 199 is forced past the second primary O-ring 168 and through the notch 136 into the channel 124 and forces the medication to the primary nozzle 142 via the passage 138. The syringe pump 1920 continues to axially move the secondary plunger 148, such that the saline is forced from the secondary chamber 199 to flush the medication from the channel 124. In this manner, the saline forces the medication through the primary lumen 816 so that all of the medication is delivered to the patient and the dual-lumen IV set 800 is primed with saline.

In some aspects, the dual-chamber syringe is pre-loaded with saline in the secondary chamber 199. In some aspects, the secondary chamber 199 is configured to receive the priming solution from the dual-lumen IV set 800, but is not utilized for reserved flushing. In some aspects, the secondary chamber 199 is configured to stop the secondary plunger 148 when receiving priming solution from the dual-lumen IV set 800 and is configured to indicate the dual-chamber syringe 110 is ready to infuse medication. In some aspects, the fluid delivery system 100 includes a valve lock to prevent fluid from being delivered to a patient during priming. In some aspects, the priming volume is selectable in 0.1 mL increments. In some aspects, the secondary plunger 148 includes a plunger handle base that rotates to allow the plunger rod to rotate and disengage while maintaining friction with a syringe pump paddle. In some aspects, the secondary plunger 148 is released automatically, instead of with a pin 209a, at a certain plunger depth so that infusion is not interrupted and does not require human interaction. In some aspects, the fluid delivery system 100 includes vents to vent residual air bubbles via air-permeable filters. In some aspects, the fluid delivery system 100 is configured to pre-set and limit the priming volume via a pin which limits plunger travel.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A dual-chamber syringe, comprising:
   an end wall comprising a channel;
   a primary plunger comprising a primary stopper, the primary stopper forming a primary chamber with the end wall;
   a secondary plunger in mechanical association with the primary plunger, the secondary plunger comprising a secondary stopper, the secondary stopper forming a secondary chamber with the primary stopper;
   a primary nozzle extending from the end wall, the primary nozzle in fluid communication with the primary chamber;
   a secondary nozzle extending from the end wall, the secondary nozzle in fluid communication with the secondary chamber; and
   an O-ring configured to isolate the primary nozzle from the secondary chamber in a pre-flushing state and to permit fluid communication between the secondary chamber and the primary nozzle via the channel in a post-flushing state.

2. The dual-chamber syringe of claim 1, wherein the secondary nozzle extends centrally from the end wall.

3. The dual-chamber syringe of claim 2, wherein the primary nozzle is radially offset from the secondary nozzle.

4. The dual-chamber syringe of claim 1, wherein the primary nozzle and the secondary nozzle are asymmetric.

5. The dual-chamber syringe of claim 1, further comprising a nozzle guide extending from the end wall and surrounding the primary nozzle and the secondary nozzle.

6. The dual-chamber syringe of claim 1, wherein the primary plunger is lockable to the secondary plunger.

7. The dual-chamber syringe of claim 1, wherein the secondary nozzle is in fluid communication with the secondary chamber via an internal tube extending from the end wall.

8. The dual-chamber syringe of claim 7, wherein the internal tube is received by a primary inner cavity of the primary plunger.

9. The dual-chamber syringe of claim 1, wherein the O-ring seals against a notch of the end wall in the pre-flushing state, wherein the notch is in fluid communication with the channel of the end wall.

10. The dual-chamber syringe of claim 9, wherein the O-ring permits fluid communication between the secondary chamber and the primary nozzle via the notch and the channel in the post-flushing state.

11. The dual-chamber syringe of claim 1, wherein fluid is forced past the O-ring to permit fluid communication between the secondary chamber and the primary nozzle in the post-flushing state.

* * * * *